United States Patent
Guillory

(10) Patent No.: US 11,738,059 B2
(45) Date of Patent: Aug. 29, 2023

(54) CONTROLLED CANNABIS DECARBOXYLATION FOR AN INFUSED SOLUBLE FAT PRODUCT

(71) Applicant: Rachel Guillory, Garland, TX (US)

(72) Inventor: Rachel Guillory, Garland, TX (US)

(73) Assignee: Rachel Guillory, Garland, TX (US)

( * ) Notice: Subject to any disclaimer, the term of this patent is extended or adjusted under 35 U.S.C. 154(b) by 75 days.

(21) Appl. No.: 17/540,237

(22) Filed: Dec. 2, 2021

(65) Prior Publication Data

US 2022/0168373 A1  Jun. 2, 2022

Related U.S. Application Data

(60) Provisional application No. 63/120,561, filed on Dec. 2, 2020.

(51) Int. Cl.

| | | |
|---|---|---|
| *A61K 36/185* | (2006.01) | |
| *A61K 9/00* | (2006.01) | |
| *A61K 47/44* | (2017.01) | |
| *A23L 33/105* | (2016.01) | |
| *A23D 7/005* | (2006.01) | |
| *A23D 7/04* | (2006.01) | |
| *B01F 33/25* | (2022.01) | |
| *B01F 27/90* | (2022.01) | |

(52) U.S. Cl.
CPC ............ *A61K 36/185* (2013.01); *A23D 7/005* (2013.01); *A23D 7/04* (2013.01); *A23L 33/105* (2016.08); *A61K 9/0056* (2013.01); *A61K 47/44* (2013.01); *B01F 27/90* (2022.01); *B01F 33/25* (2022.01); *A23V 2002/00* (2013.01); *A61K 2236/15* (2013.01); *A61K 2236/17* (2013.01); *A61K 2236/35* (2013.01); *A61K 2236/37* (2013.01); *A61K 2236/53* (2013.01)

(58) Field of Classification Search
None
See application file for complete search history.

(56) References Cited

U.S. PATENT DOCUMENTS

| | | |
|---|---|---|
| 8,980,941 B2 | 3/2015 | Hospodor |
| 9,808,494 B2 | 11/2017 | Barringer |
| 10,751,640 B1 | 8/2020 | Ferraro et al. |
| 2005/0042172 A1 | 2/2005 | Whittle |
| 2006/0068034 A1 | 3/2006 | Whittle |

FOREIGN PATENT DOCUMENTS

WO   WO 2014145490   *   9/2014

* cited by examiner

*Primary Examiner* — Michael V Meller
(74) *Attorney, Agent, or Firm* — Scott Griggs; Griggs Bergen LLP

(57) ABSTRACT

A process for controlling a decarboxylation of acidic cannabinoids for an infused soluble fat product, such as a butter product, is disclosed. In one embodiment for producing a butter product, raw *cannabis* base material is dried, pulverized, heated, and cooled to produce a decarbed *cannabis* material. The decarbed *cannabis* material is mixed with unsalted butter in an about 22:1 to and about 26:1 ratio, by weight, at ambient temperature and pressure, to produce a heterogenous butter material. The heterogenous butter material is canned and subjected to in-container thermal processing, including agitation during the thermal processing. The resulting heterogenous butter material is separated before cooling produces the butter product.

3 Claims, 3 Drawing Sheets

CONTROLLED CANNABIS DECARBOXYLATION FOR AN INFUSED SOLUBLE FAT PRODUCT

PRIORITY STATEMENT & CROSS-REFERENCE TO RELATED APPLICATIONS

This application claims priority from U.S. Patent Application No. 63/120,561, entitled "Controlled *Cannabis* Decarboxylation for an Infused Soluble Fat Product" and filed on Dec. 2, 2020, in the name of Rachel Guillory; which is hereby incorporated by reference, in entirety, for all purposes.

TECHNICAL FIELD OF THE INVENTION

This invention relates, in general, to *cannabis* decarboxylation and, in particular, to controlled *cannabis* decarboxylation of raw cannabinoids, including tetrahydrocannabinolic acid (THCA) and cannabidiolic acid (CBDA), into tetrahydrocannabinol (THC) and cannabidiol (CBD) for an infused solid fat product, such as a butter product.

BACKGROUND OF THE INVENTION

With the growing legalization of *cannabis* across the United States, various edible *cannabis* products have become more readily available, such as brownies and cookies. This has increased the demand for food grade intermediate products, such as cooking oils and butter, containing tetrahydrocannabinol (THC) and cannabidiol (CBD). Accordingly, there is a need for more processes for the controlled *cannabis* decarboxylation of raw cannabinoids.

SUMMARY OF THE INVENTION

It would be advantageous to provide processes for the controlled *cannabis* decarboxylation of raw cannabinoids. It would also be desirable to enable a chemical-based solution providing for the refinement of raw materials to make valuable fat-soluble products, such as butter, having tetrahydrocannabinol (THC) and cannabidiol (CBD). To better address one or more of these concerns, a process for controlled *cannabis* decarboxylation for an infused fat-soluble product, such as an infused butter product, is disclosed. A butter product produced according to the process is also disclosed. Additionally, a system for controlled *cannabis* decarboxylation for an infused butter product is further disclosed.

In one embodiment for the infused butter product, raw *cannabis* base material is dried, pulverized, heated, and cooled to produce a decarbed *cannabis* material. The decarbed *cannabis* material is mixed with unsalted butter in an about 22:1 to and about 26:1 ratio, by weight, at ambient temperature and pressure, to produce a heterogenous butter material. The heterogenous butter material is canned and subjected to in-container thermal processing, including agitation during the thermal processing. The resulting heterogenous butter material is separated, while heated, before cooling produces the butter product. These and other aspects of the invention will be apparent from and elucidated with reference to the embodiments described hereinafter.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which.

DETAILED DESCRIPTION OF THE INVENTION

While the making and using of various embodiments of the present invention are discussed in detail below, it should be appreciated that the present invention provides many applicable inventive concepts, which can be embodied in a wide variety of specific contexts. The specific embodiments discussed herein are merely illustrative of specific ways to make and use the invention, and do not delimit the scope of the present invention.

Figure 1:
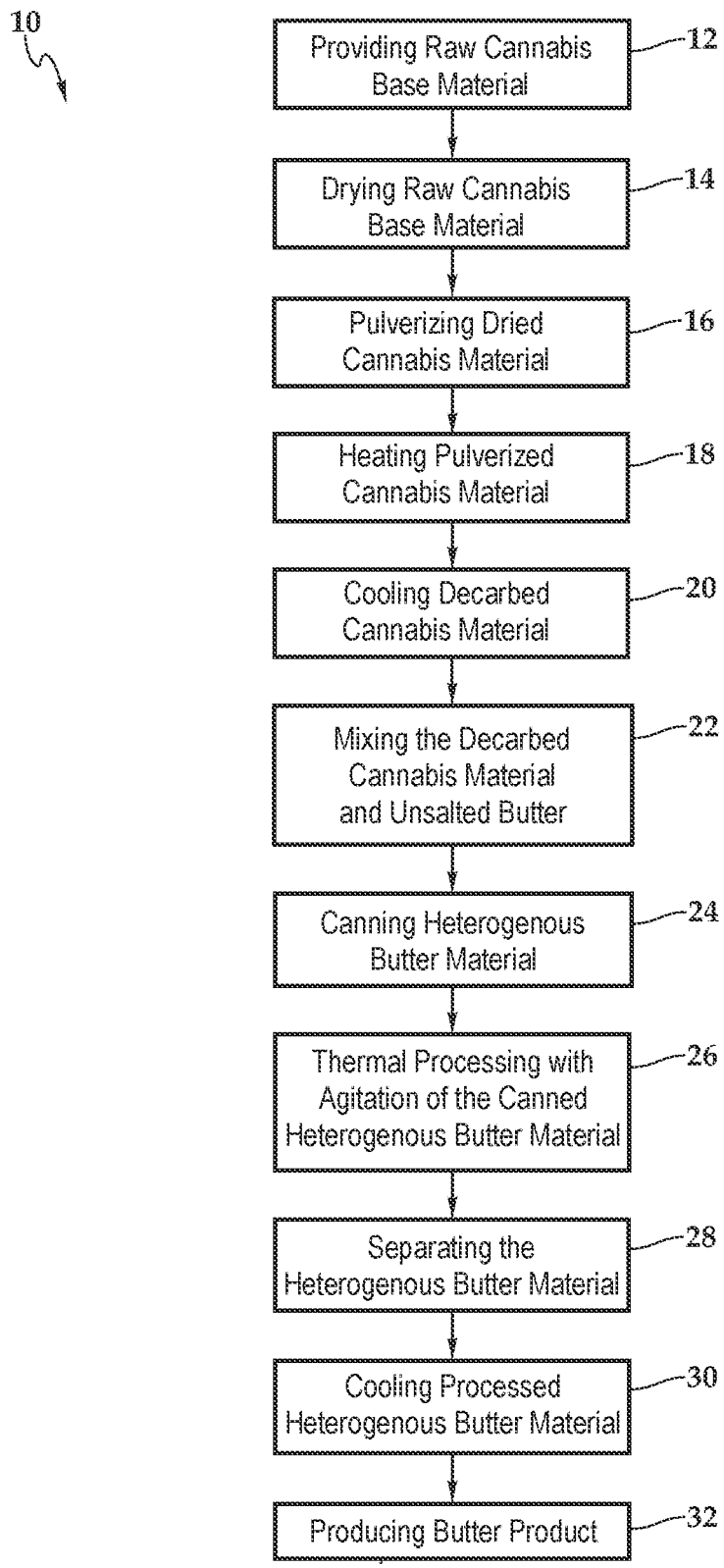
FIG. 1 is a flow chart of one embodiment of a process for controlled *cannabis* decarboxylation for an infused butter product, according to the teachings presented herein.

Referring to FIG. 1, therein is depicted one embodiment of a process 10 for controlling a decarboxylation of acidic cannabinoids for an infused soluble fat product and, in particular, an infused butter product. The acidic cannabinoids may relate to tetrahydrocannabinol (THC), cannabidiol (CBD), cannabigerol (CBG), or any other cannabinoid, for example. It should be appreciated, however, that the infused soluble fat product may also be coconut oil, ghee, medium-chain triglyceride (MCT) oil, coconut oil, vegetable oil, or another soluble fat, for example. At block 12, raw *cannabis* base material is provided. At block 14, the raw *cannabis* base material is dried at ambient temperature and pressure to produce a dried raw *cannabis* material, which has kief formed thereon. At block 16, the dried raw *cannabis* material is pulverized into small pieces to produce pulverized *cannabis* material. At block 18, the pulverized *cannabis* material is heated at a temperature of about 220° F. (104° C.) to about 230° F. (110° C.) degrees for about 40 minutes to about 55 minutes to produce a decarbed *cannabis* material. In one implementation, the pulverized *cannabis* material is heated to about 225° F. (107° C.) for 50 minutes. The heating of the pulverized *cannabis* material may also include increasing the temperature from about 250° F. (121° C.) to about 260° F. (126° C.) for 3 minutes. Often, the pulverized *cannabis* material will produce a very light smoke when the decarboxylation is complete and the decarbed *cannabis* material is produced.

At block 20, the decarbed *cannabis* material is cooled to room temperature. At block 22, the decarbed *cannabis* material is mixed with unsalted butter in an about 22:1 to an about 26:1 ratio, by weight, at ambient temperature and pressure, to produce a heterogenous butter material. At block 24, the heterogenous butter material is canned. At block 26, the canned heterogeneous butter material is subjected to thermal processing in-container by water bath canning at a sub-boiling temperature for about 3 hours to about 5 hours to produce a processed heterogenous butter material. In one implementation, the sub-boiling temperature being between about 204° F. (96° C.) to about 210° F. (99° C.). At block 26, during the thermal processing, the heterogeneous butter material is agitated at periodic intervals to cause a suspension. At block 28, following the thermal processing, the heterogenous butter material is separated while still heated. At block 30, the heterogenous butter material is cooled to produce the butter product at block 32.

Figure 2:
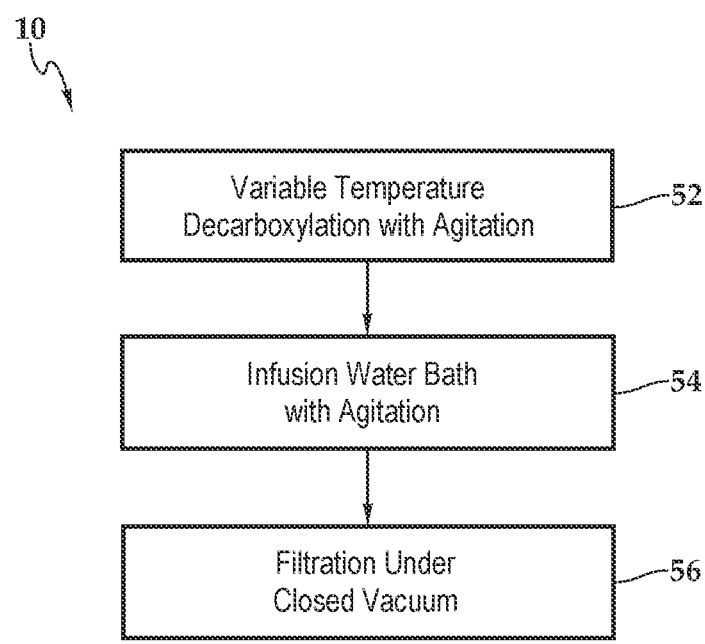
FIG. 2 is a flow chart of another embodiment of a process for controlled *cannabis* decarboxylation for an infused butter product, according to the teachings presented herein.

Referring now to FIG. 2, therein is depicted another embodiment of the process 10 for controlling a decarboxylation of acidic cannabinoids for an infused soluble fat product and, in particular, an infused butter product. In this methodology, the process is presented as occurring in three phases; namely, Phase I, Phase II, and Phase III, which are represented respectively in blocks 52, 54, 56. At block 52, which is Phase I, variable temperature decarboxylation with agitation occurs. In one embodiment, an oven capable of programmable, variable temperature at specific times with an agitator to turn over the dehydrated plant matter is utilized. This allows the oven to remain closed and retain the heat while the pulverized *cannabis* material is turned over. At block 54, which is Phase II, an infusion water bath with agitation occurs. In one embodiment, Phase II begins with a sealed jar containing fat and plant matter for the purpose of infusing the oils. The sealed jar containing fat and plant matter for infusion is then placed inside a water bath with variable temperature control. The contents of the sealed jar or, alternatively, the sealed jar, is shaken at a low speed within the water bath to promote the infusion process until the set time for the infusion end. At block 56, which is Phase III, filtration under a closed vacuum occurs. In one embodiment, a vacuum filtration apparatus includes a closed vacuum with a filter for straining plant matter from the now infused fat. The filter correlates in size to a viscosity of the fat.

Figure 3:
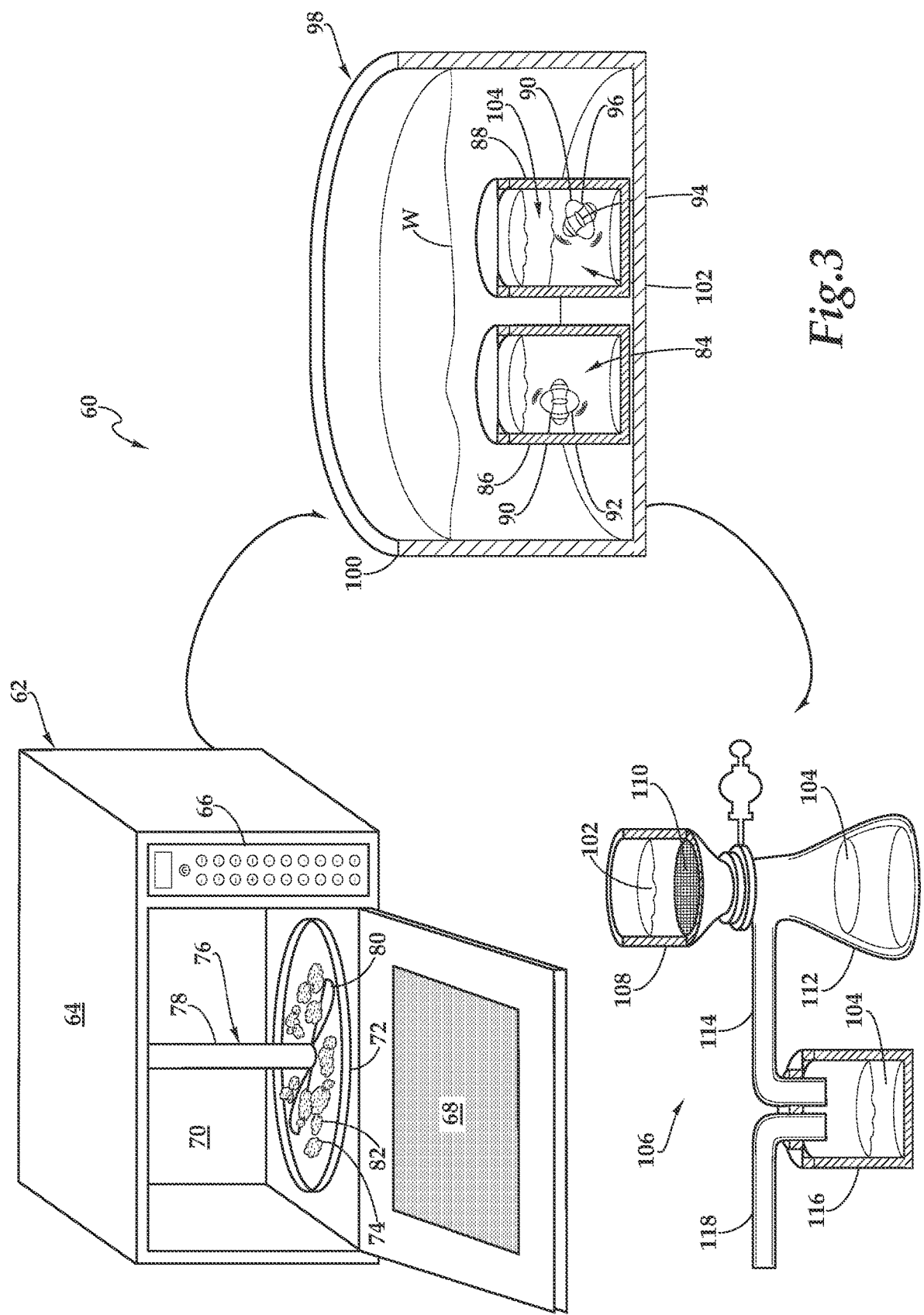
FIG. 3 is a schematic diagram, with select components in partial cross-section, of some embodiments of a system for controlled *cannabis* decarboxylation for an infused butter product, according to the teachings presented herein.

Referring now to FIG. 3, one embodiment of a system 60 for controlled *cannabis* decarboxylation for an infused butter product is illustrated. An oven 62 includes a body 64 having a control panel 66 and a door 68. The opening of the door 68 reveals a cooking chamber 70 therein. Within the cooking chamber 70, a tray 72 is located for the placement of pulverized *cannabis* material 74 therein. In some embodiments, the cooking chamber 70 includes an agitator member 76, which provides a mixing assembly for agitating the pulverized *cannabis* material 74. The agitator member 76 may include a mixer shaft 78 extending downward from a roof of the cooking chamber 70. Stirrers 80 are attached for rotational movement to the mixer shaft 78.

In operation, the pulverized *cannabis* material 74 is placed within the tray 72 of the cooking chamber 70. Using the control panel 66, a programmable, variable temperature control is set to provide, for example, a temperature of about 220° F. (104° C.) to about 225° F. (107° C.) degrees for about 40 minutes to about 55 minutes to produce a decarbed *cannabis* material 82. During heating, the agitator member 76 turn overs, via stirring in this embodiment, the pulverized *cannabis* material 74. The decarbed *cannabis* material 82 is then cooled to room temperature and mixed with unsalted butter, as previously discussed, to produce a heterogenous butter material 84.

The heterogenous butter material 84 is canned in at sealed jars 86, 88. Each of the sealed jars 86, 88 include an unattached agitator device 90 therein. In some embodiments, the unattached agitator device 90 includes a multi-faceted body 92 having a geometric center 94 and multiple arcuate surfaces 96 as well a battery compartment therein to provide a supply of power. A water bath 98 having a container 100 and water W provides thermal processing of the canned heterogeneous butter material 84 in-container at a sub-boiling temperature for about 3 hours to about 5 hours to produce a processed heterogenous butter material 102. In one embodiment, the sub-boiling temperature is between about 204° F. (96° C.) to about 210° F. (99° C.). The unattached agitator device 90 agitates, during the thermal processing, the heterogeneous butter material 84 at periodic intervals to cause a separation of the processed heterogenous butter material 102 in a suspension 104. More particularly, the unattached agitator device 90 at selective intervals, continuously and randomly collides with interior walls and a bottom of the sealed jars, either sealed jar 86 or 88, for example, to cause the suspension 104.

A vacuum filtration apparatus 106 includes a funnel 108 having a filter 110 seated therein. In some embodiments, the vacuum filtration apparatus 106 is fitted to a flask 112 having tubing 114 coupled to a trap bottle 116 and a vacuum line 118. The filter 110 may include a filter media such as filter-papers, filter cloths, cheese cloths, wire meshes, Gooch crucibles with perforated bottoms, and porcelain crucibles with porous ceramic disks, for example. The sealed jars 86, 88 may each me poured into the funnel 108 with the suction applied to separate the processed heterogenous butter material 102 from the suspension 104. The separated heterogenous butter material may then be cooled to produce the butter product. It should be appreciated that the oven 62, unattached agitator device 90, and vacuum filtration apparatus 106, as well as the other components of the system 60 are exemplary and variations in the equipment are within the teachings presented herein.

As previously mentioned, the process presented herein is not only applicable to butter products. The processes presented herein may be applied to produce any infused soluble fat products, including oils, such as coconut oil, for example, and other soluble fats. Further, the production of the decarbed *cannabis* material following the methodology of blocks 12-14 may be utilized to make other *cannabis*-based products. By way of example and not by way of limitation, the decarbed *cannabis* material may be mixed with a grain alcohol of about 120 proof to about 190 proof to produce a tincture. A jar containing a mix of the grain alcohol and decarbed *cannabis* material may be stored for approximately 6 months with agitation approximately every other day to produce a finished tincture product.

The order of execution or performance of the methods and techniques illustrated and described herein is not essential, unless otherwise specified. That is, elements of the methods and techniques may be performed in any order, unless otherwise specified, and that the methods may include more or less elements than those disclosed herein. For example, it is contemplated that executing or performing a particular element before, contemporaneously with, or after another element are all possible sequences of execution.

While this invention has been described with reference to illustrative embodiments, this description is not intended to be construed in a limiting sense. Various modifications and combinations of the illustrative embodiments as well as other embodiments of the invention, will be apparent to persons skilled in the art upon reference to the description. It is, therefore, intended that the appended claims encompass any such modifications or embodiments.

What is claimed is:

1. A process for producing an infused solid fat *cannabis* butter consisting essentially of:
   a) drying raw *cannabis* base material at ambient temperature and ambient pressure to produce a dried raw *cannabis* material, the dried raw *cannabis* material having kief formed thereon;
   b) pulverizing the dried raw *cannabis* material into small pieces to produce a pulverized *cannabis* material;

c) heating the pulverized *cannabis* material in an oven, the oven having programmable, variable temperature control to provide a temperature of about 104° C. to about 107° C. for about 40 minutes to about 55 minutes to produce a decarboxylated *cannabis* material, the oven having an agitator member therein to turn over the pulverized *cannabis* material;

d) periodically agitating, during heating, the pulverized *cannabis* material with the agitator member;

e) cooling the decarboxylated *cannabis* material to room temperature;

f) mixing the decarboxylated *cannabis* material with unsalted butter in a ratio of about 22:1 to about 26:1, by weight, at ambient temperature and pressure, to produce a heterogenous *cannabis* butter;

g) canning the heterogenous *cannabis* butter and 60%-95% ethanol in a sealed jar in a water bath to produce a tincture, at a temperature of about between about 96° C. to about 99° C.;

h) agitating, during the canning step, the processed heterogeneous *cannabis* butter at periodic intervals to cause a suspension;

i) separating the heterogenous *cannabis* butter from the suspension via the use of a vacuum filtration apparatus; and j) cooling the separated heterogenous *cannabis* butter to produce an infused solid fat *cannabis* butter.

2. The process of claim 1, wherein the heterogenous *cannabis* butter and the 60%-95% ethanol in the sealed jar is agitated by an agitator device.

3. The process of claim 1, wherein the heterogenous *cannabis* butter is separated from the suspension via the use of the vacuum filtration apparatus selected from the group consisting of filter paper, filter cloth, cheese cloth, wire mesh, a Gooch crucible with perforated bottoms and porcelain crucibles with porous ceramic disks.

\* \* \* \* \*